(12) United States Patent
Caro et al.

(10) Patent No.: US 10,369,029 B2
(45) Date of Patent: Aug. 6, 2019

(54) STENT APPARATUS AND TREATMENT METHODS

(71) Applicant: Veryan Medical Limited, Oxford (GB)

(72) Inventors: Colin Gerald Caro, London (GB);
Martin G. Burke, West Sussex (GB);
Paul Gilson, County Galway (IE);
Kevin B. Heraty, County Mayo (IE);
Nicholas Yeo, Horsham (GB)

(73) Assignee: Veryan Medical Limited, Oxford (GB)

( * ) Notice: Subject to any disclaimer, the term of this patent is extended or adjusted under 35 U.S.C. 154(b) by 0 days.

(21) Appl. No.: 15/886,629

(22) Filed: Feb. 1, 2018

(65) Prior Publication Data

US 2018/0200088 A1    Jul. 19, 2018

Related U.S. Application Data

(63) Continuation of application No. 14/774,575, filed as application No. PCT/GB2014/050822 on Mar. 14, 2014, now Pat. No. 9,907,679.
(Continued)

(51) Int. Cl.
*A61F 2/82* (2013.01)
*A61F 2/88* (2006.01)
(Continued)

(52) U.S. Cl.
CPC ............. *A61F 2/852* (2013.01); *A61F 2/82* (2013.01); *A61F 2/915* (2013.01); *A61F 2/958* (2013.01);
(Continued)

(58) Field of Classification Search
CPC ... A61F 2/82; A61F 2/88; A61F 2/852; A61B 2017/1107
(Continued)

(56) References Cited

U.S. PATENT DOCUMENTS

| 5,997,516 A | 12/1999 | Caro et al. |
| 6,039,754 A | 3/2000 | Caro |

(Continued)

FOREIGN PATENT DOCUMENTS

| GB | 2 418 362 A | 3/2006 |
| GB | 2 430 373 A | 3/2007 |

(Continued)

OTHER PUBLICATIONS

Carlier, S.G. et al., "Augmentation of wall shear stress inhibits neointimal hyperplasia after stent implantation: inhibition through reduction of inflammation?", Circulation 107(21), 2741-2746 (2003).
(Continued)

*Primary Examiner* — Suzette J Gherbi
(74) *Attorney, Agent, or Firm* — Fay Sharpe LLP (57) ABSTRACT

There is disclosed a method of treating hypoxia in tissue of a blood vessel, the method comprising placing a stent in the vessel, the stent having a center line which curves in three dimensions to promote the supply of oxygen from the blood flowing in the lumen of the stented vessel to the vessel wall. There is disclosed a method of treating a subject with diabetic atherosclerosis, the method comprising placing a stent in a blood vessel of the subject, the stent having a center line which curves in three dimensions to promote the supply of oxygen from the blood flowing in the lumen of the stented vessel to the vessel wall.

10 Claims, 10 Drawing Sheets

Related U.S. Application Data (60) Provisional application No. 61/794,803, filed on Mar. 15, 2013.

(51) Int. Cl.
    *A61F 2/852* (2013.01)
    *A61F 2/958* (2013.01)
    *A61F 2/915* (2013.01)
    *A61F 2/06* (2013.01)

(52) U.S. Cl.
    CPC ... *A61F 2002/068* (2013.01); *A61F 2002/828* (2013.01); *A61F 2210/0014* (2013.01); *A61F 2230/0091* (2013.01)

(58) Field of Classification Search
    USPC .............................................. 623/1.15–1.48
    See application file for complete search history.

(56) References Cited

U.S. PATENT DOCUMENTS

| | | | |
|---|---|---|---|
| 6,554,856 B1 | 4/2003 | Doorly et al. | |
| 7,326,240 B1 | 2/2008 | Caro et al. | |
| 7,458,985 B2* | 12/2008 | Madda | A61F 2/856 623/1.15 |
| 8,226,704 B2 | 7/2012 | Caro et al. | |
| 8,236,039 B2* | 8/2012 | Mackiewicz | A61F 2/01 623/1.1 |
| 8,236,043 B2* | 8/2012 | Caro | A61F 2/82 623/1.15 |
| 8,784,476 B2* | 7/2014 | Caro | A61F 2/07 604/103.07 |
| 8,808,354 B2* | 8/2014 | Caro | A61F 2/88 623/1.22 |
| 9,572,694 B2* | 2/2017 | Caro | A61F 2/06 |
| 2002/0179166 A1* | 12/2002 | Houston | A61F 2/06 138/39 |
| 2003/0114920 A1 | 6/2003 | Caro et al. | |
| 2005/0278017 A1* | 12/2005 | Gregorich | A61F 2/88 623/1.44 |
| 2007/0021707 A1 | 1/2007 | Caro et al. | |
| 2007/0156078 A1 | 7/2007 | Caro et al. | |
| 2008/0221665 A1* | 9/2008 | Peckham | A61F 2/88 623/1.22 |
| 2008/0262599 A1* | 10/2008 | Caro | A61F 2/82 623/1.16 |
| 2009/0248135 A1 | 10/2009 | Bruszewski et al. | |
| 2009/0293574 A1 | 12/2009 | Caro | |
| 2010/0094391 A1 | 4/2010 | Heraty et al. | |
| 2010/0094402 A1 | 4/2010 | Heraty et al. | |
| 2010/0094403 A1 | 4/2010 | Heraty et al. | |
| 2010/0179641 A1* | 7/2010 | Ryan | A61F 2/2418 623/1.15 |
| 2010/0286759 A1 | 11/2010 | Taylor et al. | |
| 2011/0040371 A1* | 2/2011 | Hanssen | A61F 2/88 623/1.22 |
| 2011/0251671 A1 | 10/2011 | Heraty et al. | |
| 2011/0257673 A1* | 10/2011 | Heraty | A61F 2/958 606/194 |
| 2012/0283819 A1 | 11/2012 | Taylor et al. | |
| 2013/0261733 A1* | 10/2013 | Su | A61F 2/88 623/1.15 |
| 2014/0135900 A9 | 5/2014 | Heraty et al. | |
| 2014/0277352 A1* | 9/2014 | Caro | A61F 2/82 623/1.11 |
| 2015/0066134 A1* | 3/2015 | Bonhoeffer | A61F 2/2418 623/1.16 |
| 2016/0324667 A1* | 11/2016 | Heraty | A61F 2/91 |

FOREIGN PATENT DOCUMENTS

| | | |
|---|---|---|
| WO | WO 00/32241 | 6/2000 |
| WO | WO 2006/032902 A1 | 3/2006 |
| WO | WO 2007/082533 A1 | 7/2007 |
| WO | WO 2008/125842 A1 | 10/2008 |
| WO | WO 2010/041038 A1 | 4/2010 |
| WO | WO 2010/041039 A1 | 4/2010 |
| WO | WO 2010/041040 A1 | 4/2010 |
| WO | WO 2010/128311 A1 | 11/2010 |

OTHER PUBLICATIONS

Caro, C.G. et al., "Non-planar curvature and branching of arteries and non-planar-type flow", Proc Royal Soc 452, 185-197 (1996).
Caro, C.G. et al., "Arterial Stent Intimal Hyperplasia: Role of Hypoxia and Blood-Wall Oxygen Transport", Physiology 2011, Oxford. Proc Physiol Soc 23, C79, (Abstract) (2011), 2 pages.
Caro, C.G. et al., "Arterial Stent-Associated Intimal Hyperplasia and Wall Hypoxia", Imperial College London (Mar. 28, 2012).
Caro et al., "Intimal Hyperplasia following implantation of helical-centreline and straight-centreline stents in common carotid arteries in healthy pigs: influence of intraluminal flow" J R Soc Interface 10: 20130578, http://dx.doi.org/10.1098/rsif.2013.0578, 9 pages (2013).
Cheema, A.N. et al., "Adventitial microvessel formation after coronary stenting and the effects of SU11218, a tyrosine kinase inhibitor", J Am CollCardiol 47(5),1067-1075 (2006).
Coppola, G. et al., "Oxygen mass transfer in a model three-dimensional artery", J RS Interface 5, 1067-1075 (2008).
Dake, M.D. et al., "Polymer-free paclitaxel-coated Zilver PTX Stents—evaluation of pharmacokinetics and comparative safety in porcine arteries", J Vasc Interv Radiol 22(5), 603-610 (2011).
Dember, M. et al., "Early fistula failure: Back to basics", American Journal of Kidney Diseases 50(5), 696-699 (2007).
Guzman, L.A. et al., "Role of intimal hyperplasia and arterial remodeling after balloon angioplasty", ATVB 16, 479-487 (1996).
How, T.V. et al., "Swirling flow pattern in a non-planar model of an interposition veincuff anastomosis", Med Eng Phys 28(1), 27-35 (2006).
Lee, T. et al., "Advances and New Frontiers in the Pathophysiology of Venous Neointimal Hyperplasia and Dialysis Access Stenosis", Adv Chronic Kidney Dis 16(5), 329-338 (2009).
Lemson, M.S. et al., "A new animal model to study intimal hyperplasia in arteriovenousfistulas", Journal of Surgical Research 85(1), 51-58 (1999).
Litster, S. et al., "Convective mass transfer in helical pipes: effect of curvature and torsion", Heat and Mass Transfer 42(5), 387-397 (2005).
Maurice, G. et al., "Modeling of elastic deformation and vascular resistance of arterial and venous vasa vasorum", J.Malad.Vasc 23(4), 282-288 (1998).
Mauro, M.A., "The battle of intimal hyperplasia in the war against femoropopliteal disease", Radiol 231, 299-301 (2004).
Moreno, Perdro R., et al., "New Aspects in the Pathogenesis of Diabetic Atherorthrombosis", Journal of the American College of Cardiology, vol. 44, No. 12, (2004).
Moreno, Pedro R. et al., "Plaque neovascularization: defense mechanisms, betrayal, or a war in progress", Analysis of the New York Academy Sciences 1254, (Apr. 30, 2012).
Morice, M.C. et al. For the RAVEL Study Group, "A Randomized Comparison of a Sirolimus-Eluting Stent with a Standard Stent for Coronary Revascularization", The New England Journal of Medicine 346(23), 1773-1780 (2002).
Nikol, S. et al., "Restenosis in human vein bypass grafts", Atherosclerosis 139(1), 31-39 (1998).
PAM 049 Issue 01 VIVA 2013 presentation.
Rogers, C. et al., "Balloon-Artery Interactions During Stent Placement : A Finite Element Analysis Approach to Pressure, Compliance, and Stent Design as Contributors to Vascular Injury", Circulation Research 84, 378-383 (1999).
Rotmans, J.I. et al., "Rapid, arteriovenousgraft failure due to intimal hyperplasia: A porcine, bilateral, carotid arteriovenous graft model", Journal of Surgical Research 113(1), 161-171 (2003).
Santilli, S.M. et al., "Transarterial wall oxygen gradients at the deployment site of an intra-arterial stent in the rabbit", American Journal of Physiology—Heart and Circulatory Physiology 279, H1518-H1525 (2000).

(56) References Cited

OTHER PUBLICATIONS

Shinke, T. et al., "Novel helical stent design elicits swirling blood flow pattern and inhibits neointima formation in porcine carotid arteries", Circulation 118, S_1054 (2008).
Shweiki, D. et al., "Vascular endothelial growth factor induced by hypoxia may mediate hypoxia-initiated angiogenesis", Nature 359, 843-845 (1992).
Tarbell, J.M., "Mass transport in arteries and the localization of atherosclerosis", Ann Rev Biomed Eng 5, 79-118 (2003).
Timmins, L.H. et al., "Increased Artery Wall Stress Post-Stenting Leads to Greater Intimal Thickening", Lab Invest 91(6), 955-967 (2011).
Tretinyak, A.S. et al., "Supplemental oxygen reduces hyperplasia after intra-arterial stenting in the rabbit", Journal of Vascular Surgery 35, 982-987 (2002).
Wang, Y. et al., "Venous stenosis in a pig arteriovenous fistula model—anatomy, mechanisms and cellular phenotypes", Nephrology Dialysis Transplantation 23(2), 525-533 (2008).
Zeller, T. "MIMICS Clinical Trial: First clinical experience with Veryan BioMimics 3DTM stent", Vascular interventional advances (VIVA), Las Vegas (2012).
Zhu et al., "Cataloging the geometry of the human coronary arteries: a potential tool for predicting risk of coronary artery disease", International Journal of Cardiology 135, 43-52, (2009).
http://wwwf.imperial.ac.uk/ssherw/spectralhp/papers/PhDThesis/A_CooksonPhDThesis.pdf (Abstract only) (published 2009).
http://www.physoc.org/proceedings/abstract/Proc%20Physiol%20Soc%2023C79 (Abstract only, abstract published 2011).
International Search Report of International Application No. PCT/GB2014/050822 dated Jul. 9, 2014, 5 pages.
Written Opinion of the International Searching Authority of International Application No. PCT/GB2014/050822 dated Jul. 9, 2014, 6 pages.

* cited by examiner

STENT APPARATUS AND TREATMENT METHODS

This application is a continuation of U.S. patent application Ser. No. 14/774,575 which was filed on Sep. 10, 2015. That application, in turn, is the entry into the national phase in the U.S. of International Application Serial No. PCT/GB2014/050822 which was filed on Mar. 14, 2014 and which claims priority to U.S. Provisional Patent Application Ser. No. 61/794,803 which was filed on Mar. 15, 2013.

BACKGROUND

The invention relates to a stent apparatus and to a method of treating hypoxia in vascular tissue, and to treatment and stenting methods of subjects with diabetes mellitus.

Blood vessel walls are comprised of living cells which are metabolically active and therefore require a supply of nutrients including oxygen. In the absence of disease, cells in blood vessel walls receive oxygen from the lumen via transmural diffusion of oxygen from the blood at the inside wall of the vessel. Capillary-like microscopic vessels that originate in the main vessel or another vessel and spread through the adventitia (outer layer) of the vessel, known as adventitial micro vessels, provide the outer portion of the vessel tissue with a supply of blood and consequently oxygen. Cells in tissue closer to the lumen wall of the vessel are more reliant on the transmural diffusion mechanism for their supply of oxygen.

Early fatty streak to advanced atherosclerotic lesions also contain inflammatory cells which exhibit a high level of metabolic activity requiring a continuous oxygen supply. Hypoxic conditions can emerge particularly at the intima-media transition due to the development of extra-cellular matrix in the intima as a result of previous inflammatory episodes in the vessel wall. In hypoxic conditions the metabolically active cells express hypoxia inducible factor (HIF) which triggers a defense mechanism which attempts to restore normoxic conditions and prevent hypoxia induced necrosis and loss of tissue integrity. A key component of this defence mechanism is angiogenesis.

Angiogenesis, which is the formation of new blood vessels, may be triggered by homeostatic imbalances including hypoxia. It may be classified as physiological angiogenesis in a normal state, being fundamental for development, reproduction and repair of blood vessels or pathological angiogenesis which is persistent due, for example, to the inability to restore normoxic conditions. Hypoxia is associated with inflammation and particularly an increased metabolic demand due to macrophage infiltration. Vessel wall hypoxia can be accentuated due to an accumulation of fatty streaks or extracellular matrix in the intima (the innermost lining of the vessel), which limits oxygen diffusion to the portion of the vessel wall exterior to the lesion. The resulting presence of HIF in the nuclei of macrophages triggers the upregulation of a number of angiogenic factors including vascular endothelial growth factor (VEGF) which initiates the development of new vessels which can improve the local oxygen supply and allow tissue repair. In physiological angiogenesis, after healing has taken place, the process is reversible and angiogenesis regresses. Therefore physiological angiogenesis occurs focally and is a self-limiting process.

However, pathological angiogenesis involves the persistence over a significant time period of angiogenic stimuli, including hypoxia. The persistent expression of VEGF results in immature neo-vessel formation with poorly formed microendothelium exhibiting incomplete gap junctions which leak red blood cells into the surrounding tissue in a process termed intra-plaque haemorrhage. Red blood cells are rich in cholesterol so this haemorrhage leads to lipid core expansion and increased plaque burden. Plaques which exhibit intra-plaque haemorrhage exhibit rapid progression and are associated with an increased occurrence of clinical events, as discussed in the paper "Plaque neovascularization: defense mechanisms, betrayal, or a war in progress" by Moreno et al. 2012, Annals of the New York Academy of Sciences 1254 (2012) 7-17.

The above mechanisms suggest a central role for vessel wall hypoxia in the development and progression of occlusive vascular disease. Such plaques are commonly treated by endovascular interventions including the placement of a stent to expand the vessel at the site of the blockage and maintain patency.

BRIEF SUMMARY

According to a first aspect of the invention, there is provided a method of treating hypoxia in tissue of a blood vessel, the method comprising placing a stent in the vessel, the stent having a centre line which curves in three dimensions to promote the supply of oxygen from the blood flowing in the lumen of the stented vessel to the vessel wall.

Conventional stents are used to treat vessel blockages but may themselves induce hypoxia in the vessel wall tissue which, as discussed above, is a trigger for angiogenesis. Thus although the stent is used as a treatment for a blockage which may itself be caused by hypoxia and is effective in doing so by expanding the flow lumen, the stent does not mitigate the cause of the hypoxia. As a result, intimal hyperplasia is a principal cause of obstruction and failure of stented vessels. The characteristics of intimal hyperplasia may differ in the different situations, but the process is generally regarded as comprising vessel wall thickening and luminal narrowing, caused by the proliferation and accumulation of cells, including smooth muscle cells and extracellular matrix in the intima. Measures adopted to prevent intimal hyperplasia development have included the administration of antithrombotic agents, anticoagulants, ACE inhibitors, cytotoxic agents, vascular endothelial growth factor and brachytherapy, but none has been successful.

Drug eluting stents, which are stents coated with antiproliferative agents, have attracted much attention. Improved patency is reported, as compared with bare metal stents, however concerns remain about the long term effects of the polymeric coatings which form the matrix into which the drugs are loaded. Drug elution follows a time-limited course and ultimately the vessel is exposed to risk of chronic irritation or injury from the stent without antiproliferative mitigation.

In a straight stent it is likely that the boundary layer at the vessel wall becomes depleted of oxygen relative to the main flow thereby limiting the transmural diffusion of the blood at the wall. It has also been observed that the radially expansive force induced by the stent causes compression of adventitial micro vessels, reducing their cross-sectional area and flow, further limiting the ability to provide the outer portion of the vessel tissue with a supply of blood and hence oxygen.

By using a stent with a centre line which curves in three dimensions, for example a stent which has a helical centre line, there is improved intraluminal mixing and a reduction in the thickness of the boundary layer, i.e. the boundary layer in the straight stent is thicker as the gradient of velocity close to the wall is smaller than that observed in a stent which curves in three dimensions.

The effect of the stent having a centre line which curves in three dimensions is that oxygen concentration levels immediately at the vessel wall are increased, thereby improving the transmural diffusion of oxygen from the blood at the inside wall of the vessel. The effect of this is to reduce the angiogenic stimulus, leading to fewer adventitial micro vessels, reduced inflammation (hence reduced oxygen demand) and intra-plaque haemorrhage, slowing or possibly halting atherosclerotic progression. Furthermore swirling flow serves to limit intimal thickening and restenosis presumably through mechanisms including reduction in oxygen demand (reduced inflammation) and increasing supply.

In this specification consideration has been given to the involvement of luminal wall mass transport, as discussed further below.

Stenting can render arteries locally hypoxic. In-stent intimal cross sectional area was found to be highly correlated with adventitial micro vessel number and adventitial micro vessel number can be considered representative of tissue hypoxia; it increases after stenting and hypoxia is a major stimulus for angiogenesis. Intraluminal swirling can enhance wall shear stress. But, it can additionally increase intraluminal blood-vessel wall transport of molecular species whose intraluminal blood-wall mass transport is fluid-phase controlled, including oxygen. Thus, swirling can enhance wall shear rate and, by virtue of intraluminal mixing, convectively enhance intraluminal blood-vessel wall mass transport.

Based on these observations and the recognition that arterial wall mass transport derives from both adventitial micro vessel and intraluminal blood, this specification discusses quantifying the adventitial micro vessel in three dimensional (3D) centre line stented and straight centre line stented arteries. Adventitial micro vessel density is found to be significantly lower in the former vessels. In the light of the findings above, it is reasonable to advance the proposal that adventitial micro vessel density is representative of wall hypoxia. It is furthermore reasonable to advance the hypothesis that the lesser occurrence of intimal hyperplasia in 3D centre line stented than straight centre line stented arteries results from intraluminal mixing having enhanced blood-wall mass transport, thus mitigating stent-induced wall hypoxia.

Stenting can be expected to alter the porosity and permeability of the arterial wall. Studies of the immediate effects of arterial stenting on the morphology of adventitial micro vessels have not been found, but it has been found that distension of arteries by increase of their transmural pressure caused adventitial micro vessel cross-sections to change from circular to elliptical, their hydraulic resistance to rise, and their flow to fall, potentially impairing wall nutrition. Stenting will not increase adventitial micro vessel intraluminal pressure, in the manner that elevation of arterial transmural pressure in situ will. It could therefore affect adventitial micro vessel morphology and flow more severely than distension of vessels by pressurization.

It has been proposed in several patent publications, namely WO 00/32241, WO 2007/082533, WO2006/032902, WO2010/041040, WO2010/041039, WO2010/041038 and WO2010/128311 (the contents of all of which are incorporated herein by reference), that intimal hyperplasia can be significantly reduced by using a stent having a centre line curving in three dimensions.

However, these publications do not disclose that stenting can render arteries locally hypoxic, nor that a stent with a centre line curving in three dimensions can inhibit hypoxia, nor that additional micro vessel numbers can be considered representative of hypoxia. Stents are usually provided in a collapsed condition until they have been located at the treatment site, where they are expanded. The stent used in the methods described herein may be balloon-expandable. Thus the stent may be provided with a balloon to expand it from the collapsed to the expanded condition. The stent may be made of a shape memory material, such as a shape memory alloy, for example nitinol. Stents made of shape memory materials may be delivered in a collapsed condition and then expanded, for example by removing an external radial constraint, so that they expand at the treatment site. A shape memory stent may in some circumstances be provided with a balloon to assist expansion.

When the stent of the invention is expanded ex vivo it will generally have a centre line which curves in three dimensions. When it is expanded in vivo, it will to some extent be constrained from adopting its fully expanded ex vivo geometry due to the counteracting constraining action of the vessel. Whilst this may to some extent reduce the three dimensional curvature of the stent, three dimensional curvature is still maintained.

Preferably the stent when expanded ex vivo has a helical centre line. When the stent is expanded in vivo the constraining action of the vessel will to some extent modify the helical geometry, for example reducing the curvature. This can result for example from a reduction in the helical amplitude and/or an increase in the pitch. There may then be variations in the curvature over the length of the stent, due to variations in the helical amplitude and/or helical pitch.

The stent may impose its three dimensional geometry on the vessel. The vessel may be caused by the stent to adopt the same three dimensionally curved centre line as the stent. Known stents which adapt their shape to existing geometry could just be reproducing the geometry which originally led to the occurrence of a lesion or, even worse, could be accentuating conditions which led to the occurrence of the lesion.

The recognition in this specification that conventional stents contribute to the phenomenon of hypoxia and that the use of stents with a centre line curving in three dimensions can treat hypoxia, opens up the use of particular stent geometries with certain patient groups.

According to a second aspect of the invention, there is provided a method of treating a subject with diabetic atherosclerosis, the method comprising placing a stent in a blood vessel of the subject, the stent having a centre line which curves in three dimensions to promote the supply of oxygen from the blood flowing in the lumen of the stented vessel to the vessel wall.

Subjects with diabetes mellitus often develop diabetic atherosclerosis. They can suffer from flow limiting atherosclerotic disease. A contributing factor to this development is hypoxia in the vessel tissue. By using a stent which itself treats or inhibits hypoxia, restenosis in patients with diabetic atherosclerosis or diabetes mellitus may be reduced.

According to a third aspect of the invention, there is provided a method of treating hypoxia in tissue of a blood vessel in which a stent is already disposed, the method comprising placing an expandable member in a collapsed condition thereof radially inwardly of the stent in the vessel, and expanding the expandable member from the collapsed condition to an expanded condition in which the expandable member has a centre line which curves in three dimensions, so as to cause the stent to adopt a shape in which it also has a centre line which curves in three dimensions.

Once the stent has been caused to adopt a shape in which it has a centre line which curves in three dimensions, this alters the shape of the flow lumen of the vessel to promote the supply of oxygen from the blood flowing in the lumen of the stented vessel to the vessel wall. Swirl flow may be promoted in the flow lumen. The thickness of the boundary layer may be reduced and mass transport, particularly oxygen, between the blood and the vessel wall may be increased. This can treat hypoxia in the vessel wall.

It will be understood that post dilation of a stent with an expandable member may be carried out to treat hypoxia.

The expandable member may be a balloon.

The centre line of the stent and that of the expandable member after the expandable member has been expanded from the collapsed condition to the expanded condition may be the same.

The centre line of the expandable member when expanded ex vivo to the expanded condition may be a helical centre line. When the expandable member is expanded in the stent there may be resistance from the stent and the vessel wall with the result that the curvature along the length of the stent may vary. For example the curvature may be reduced compared to that which the expandable member would adopt if expanded ex vivo. The helical amplitude may be decreased and/or the pitch may be increased, such variations in either of these parameters resulting in reduced curvature in vivo compared to ex vivo.

After the stent has been caused to adopt a shape in which it has a centre line which curves in three dimensions, the expandable member may be collapsed and removed. The stent may retain the shape imparted to it by the expandable member. The stent may retain the shape by having been plastically deformed.

The stent which is to be expanded may comprise stainless steel or cobalt chromium, magnesium based alloys or biodegradable polymeric materials. It will be understood that other plastically deformable materials may be used.

According to a fourth aspect of the invention, there is provided a method of treating a subject for whom blood vessel stenting is indicated, the method comprising placing a drug eluting stent in the vessel, the stent having a centre line which curves in three dimensions.

The invention also provides a drug eluting stent having a centre line which curves in three dimensions.

Swirl flow may be promoted in the flow lumen of the vessel stented with the drug eluting stent. The thickness of the boundary layer may be reduced.

Secondary flow (i.e. the component of the flow transverse to the main axial flow) can move the drug from the immediate vicinity of the stent to the areas between the members, such as struts, which form the stent. Thus the drug can act to inhibit intimal growth more effectively in these areas of the vessel wall which are not in contact with the stent. This can be contrasted with conventional straight stents where there is relatively little secondary flow so the drug eluted from the stent reaches these areas to a lesser extent.

The vessel may be a main vessel and a branch vessel may extend from the main vessel, and the stent may be placed in the main vessel so that at least a portion of the stent extends in the main vessel upstream of the branch vessel. This allows the stent to influence the flow upstream of the branch vessel, which may also be considered as a collateral or daughter vessel). Secondary flow in the main vessel can allow the drug to be swept into the bulk flow from the drug eluting stent and carried downstream into the branch vessel. After stenting the angle between the main branch and the branch vessel often changes, which can result in the development of a stenosis at the proximal end of the collateral vessel. The drug which is now in the bulk flow can reduce the propensity for this proximal disease in the collateral vessel to develop. The branch vessel may be unstented. The method may comprise stenting the branch vessel. A second stent in the branch vessel may not be a drug eluting stent. It may be for example a bare metal stent. Secondary flow in the main vessel can allow the drug to be swept into the bulk flow from the drug eluting stent and carried downstream into the branch vessel, where it can act in the region of the second stent to provide a therapeutic benefit to the stented branch vessel. It may for example inhibit intimal ingrowth in the branch vessel.

The stent in the main vessel may extend therein downstream of the branch vessel. The stent may therefore extend both upstream and downstream of the junction with the branch vessel. Flow from the main vessel may enter the branch vessel by passing though openings in the stent, such openings being conventional in stents.

According to a fifth aspect of the invention, there is provided a method of treating a subject for whom blood vessel stenting is indicated, wherein the vessel is a main vessel and a branch vessel extends from the main vessel, the method comprising placing the stent in the main vessel so that at least a portion of the stent extends in the main vessel upstream of the branch vessel, and the stent having a centre line which curves in three dimensions.

According to a sixth aspect of the invention, there is provided a method of treating a blood vessel branching from another vessel having a stent therein with at least a portion of the stent being upstream of the branch vessel, the method comprising placing an expandable member in a collapsed condition thereof radially inwardly of the stent in the vessel, and expanding the expandable member from the collapsed condition to an expanded condition in which the expandable member has a centre line which curves in three dimensions, so as to cause the stent to adopt a shape in which it also has a centre line which curves in three dimensions.

By providing a stent having a centre line which curves in three dimensions in a main vessel so that at least a portion of the stent extends in the main vessel upstream of a branch vessel, or by causing a stent already in a main vessel to adopt a shape in which it has a centre line which curves in three dimensions, secondary flow in the branch vessel may be promoted to provide a therapeutic benefit to the branch vessel. The use of a conventional stent in a main vessel can result in a change of angle between the main vessel and the branch vessel, which may lead to a reduced flow rate and the development of a stenosis in the branch vessel. The promotion of secondary flow in the main branch upstream of the branch vessel may increase flow rate in the branch vessel and may inhibit development of a stenosis in the branch vessel.

According to a seventh aspect of the invention, there is provided a method of treating a subject for whom blood vessel stenting is indicated, comprising identifying a treatment site, determining whether natural vessel geometry at that treatment site will impart right-handed swirl flow or left-handed swirl flow to the blood flow along the vessel, and selecting for placement at the treatment site a stent having a centre line with three-dimensional curvature, the selected stent having right-handed curvature if the vessel has been determined to naturally impart right handed swirl flow and the selected stent having left-handed curvature if the vessel has been determined to naturally impart left-handed swirl flow.

The invention also provides apparatus comprising a plurality of stents each having a centre line curving in three dimensions, the plurality of stents including at least one stent with a centre line having right-handed curvature and at least one stent with a centre line having left-handed curvature.

The stent with right-handed curvature may be for use in a vessel which has been determined to naturally impart right handed swirl flow, and the stent with left-handed curvature may be for use in a vessel which has been determined to naturally impart left-handed swirl flow. When a clinician wishes to stent a vessel, the apparatus provides a choice of using a right-hand curved stent or a left-hand curved stent. A stent may be selected as appropriate to complement the natural direction of swirl and not to tend to cancel it.

The choice can be made based on whether the site at which the stent is to be located is one where there will be natural right-handed swirl flow or natural left-handed swirl flow of the blood flow along the vessel. The handedness of the swirl flow can be determined by scanning the vessel by known scanning methods, such as X-ray scanning transverse colour Doppler ultrasound, Computer Tomography (CT), Magnetic Resonance Imaging (MRI) or C-Arm Cone Beam CT, and then the appropriate stent may be selected. Alternatively the handedness can be determined by reference to the following examples.

Examples of vessels which commonly have right-handed curvature are the left iliac artery, the left iliac vein, the left femoropopliteal artery, the left femoropopliteal vein, the left coronary artery, and the left anterior descending artery. Examples of vessels which commonly have left-handed curvature are the right iliac artery, the right iliac vein, the right femoropopliteal artery, the left coronary circumflex and the right femoropopliteal vein.

The above examples are not exhaustive and of course there are other treatment sites which can benefit from selecting a stent with three dimensional curvature of the appropriate curvature. It is also understood that handedness of specific vessels may vary from patient to patient.

Commonly where a vessel bifurcates, the geometry of the bifurcation is such that the flow downstream of the bifurcation in both branches is swirling flow.

Therefore a stent placed downstream of a bifurcation can be selected with the appropriate three dimensional curvature handedness.

Right-handed curvature of the centre line means clockwise curvature and left-handed curvature means counterclockwise curvature. Clockwise curvature involves clockwise rotation of the centre line of the stent as viewed in a direction receding away form the viewer, and counterclockwise curvature involves counterclockwise rotation of the centre line of the stent as viewed in a direction receding away from the viewer.

The apparatus may comprise a plurality of right-handed curved stents and a plurality of left-handed curved stents. The right-handed curved stents may be all the same size, or there may be different sizes. The left-handed curved stents may be all the same size, or there may be different sizes. The diameters and/or lengths of the stents may be different.

BRIEF DESCRIPTION OF THE DRAWINGS

Certain preferred embodiments of the invention will now be described by way of example and with reference to the accompanying drawings, in which.

DETAILED DESCRIPTION

Figure 1:
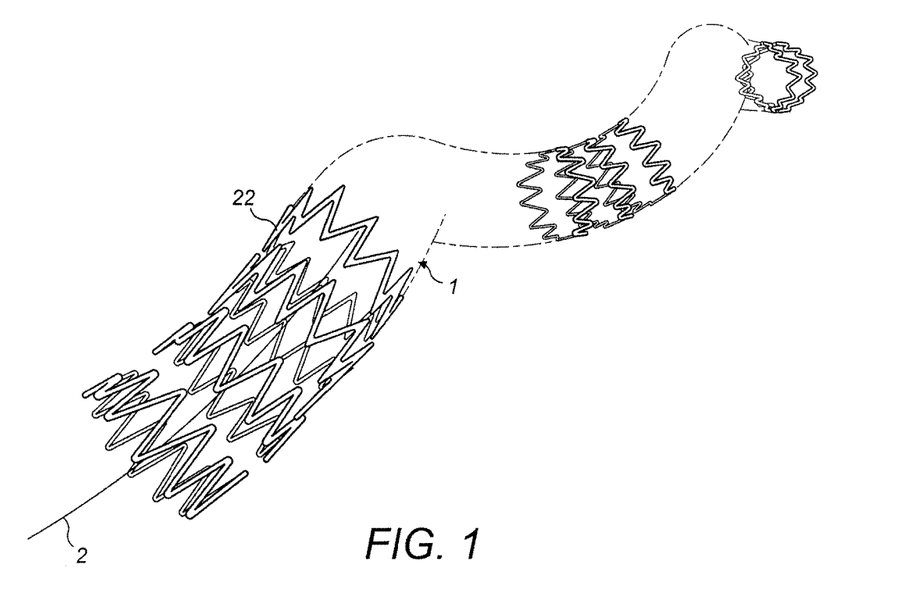
FIG. 1 is a perspective view of an embodiment of a helical stent in accordance with the invention.

FIG. 1 shows a self-expanding stent 1 made from a shape memory alloy, in this case nitinol. The stent 1 has a helical centre line 2. The stent 1 comprises struts 22.

Figure 2:
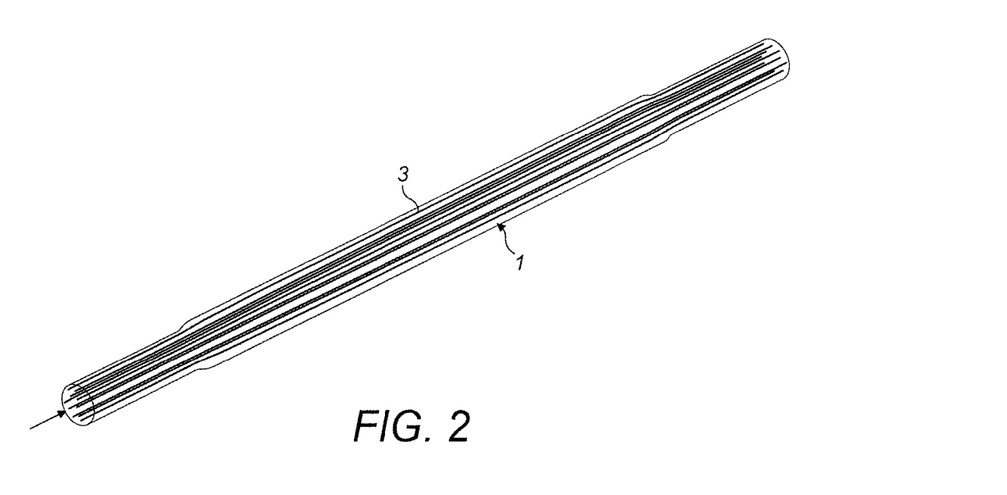
FIG. 2 is a perspective view illustrating flow in a straight stent.
Figure 3:
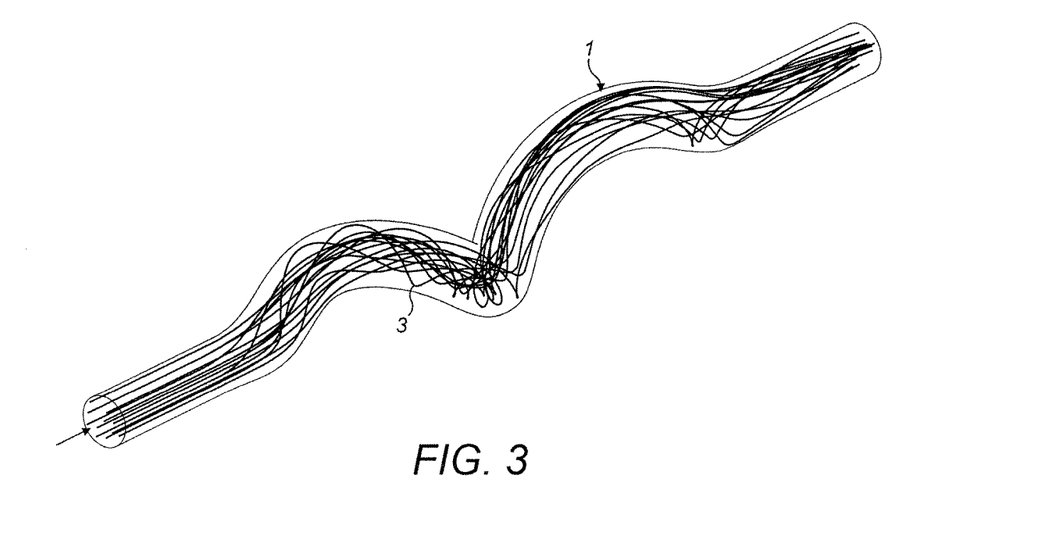
FIG. 3 is a perspective view illustrating flow in a helical stent.

FIGS. 2 and 3 show the flow in straight and helical stented arteries respectively. The flow lines 3 in the straight stented artery shown in FIG. 2 are generally straight, whereas the flow lines 3 in the helical stented artery show a swirling pattern illustrating how fluid at the vessel wall is transported towards the centre of the flow and vice versa.

Figure 4:
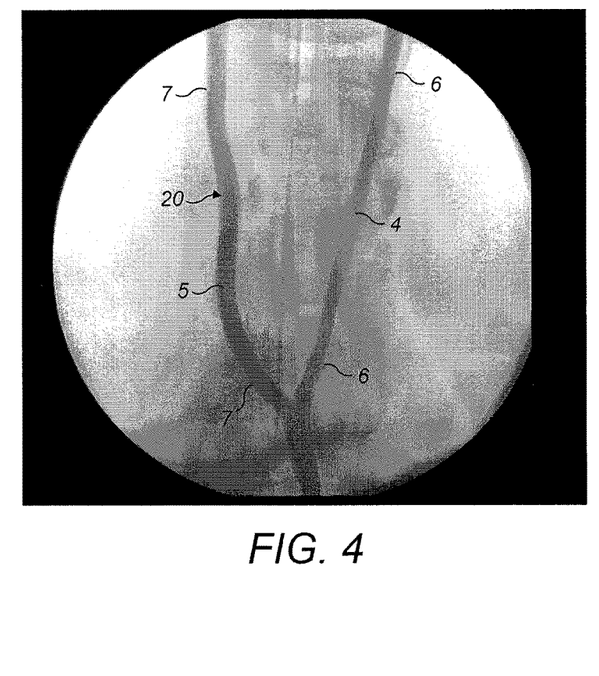
FIG. 4 shows a pair of porcine carotid arteries implanted with straight and helical stents.

FIG. 4 shows an angiogram image of a pair of porcine carotid arteries 20 which have been stented. The straight stented artery 4 is shown on the right hand side, having downstream and upstream ends 6. The helical stented artery 5 is shown on the left hand side, having downstream and upstream ends 7. It can be seen that the straight stented artery is substantially straight and that the helical stented artery exhibits three dimensional curvature.

Figure 5:
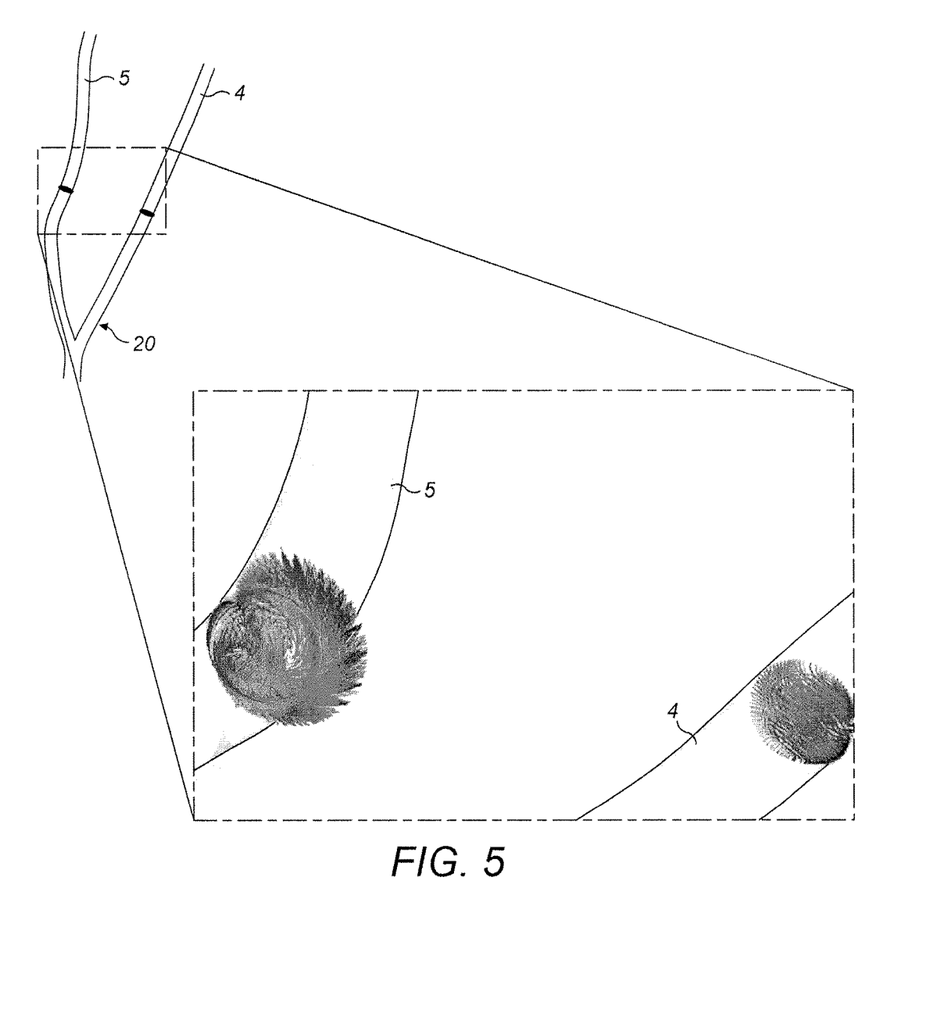
FIG. 5 shows a computational fluid dynamics (CFD) simulation of flows in porcine carotid arteries stented with straight and helical stents.

FIG. 5 shows vector diagrams produced by a computational fluid dynamic simulation of flow in stented arteries. At the upper left of the drawing the porcine carotid arteries are shown, and portions thereof are shown to an enlarged scale on the right of the drawing. The straight stented artery is indicated at reference 4 and the helical stented artery is indicated at reference 5. The vectors themselves are shown as "brush" like images, with each "bristle" of the brush being a flow vector. Each image represents the flow across the transverse section of the respective artery at the region shown. Each vector shows the so-called secondary component of the flow field, i.e. the component of flow at the relevant point on the transverse section which is perpendicular to the longitudinal axis of the artery, along which there is the primary flow. It will be seen that the helical stented artery 5 exhibits a distinctive swirling pattern and that this swirl flow involves relatively high secondary flow velocities, indicated by the relatively large length of the vectors, near the inside (medial) wall of the artery. On the other hand the near wall vector length for the straight stented artery 4 is relatively small, indicating slower secondary near wall flow velocities.

Figure 6A:
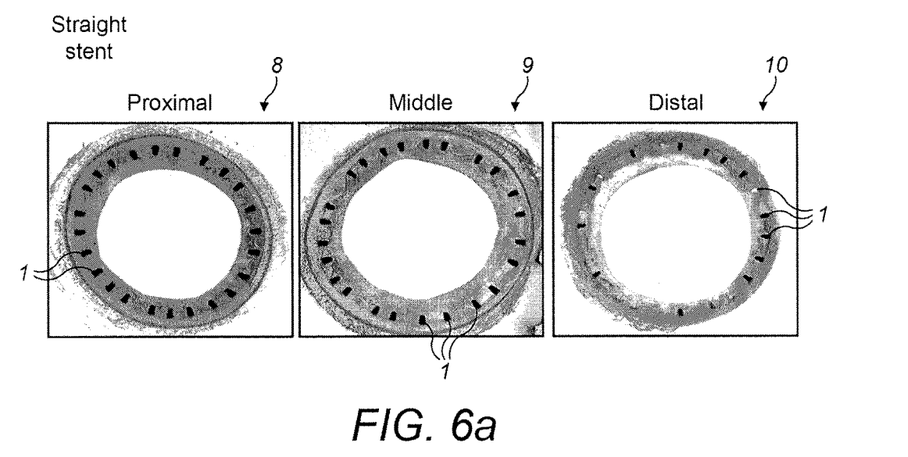
FIGS. 6a and 6b show transverse histology sections of proximal, middle and distal segments of carotid arteries one month after stent deployment.
Figure 6B:
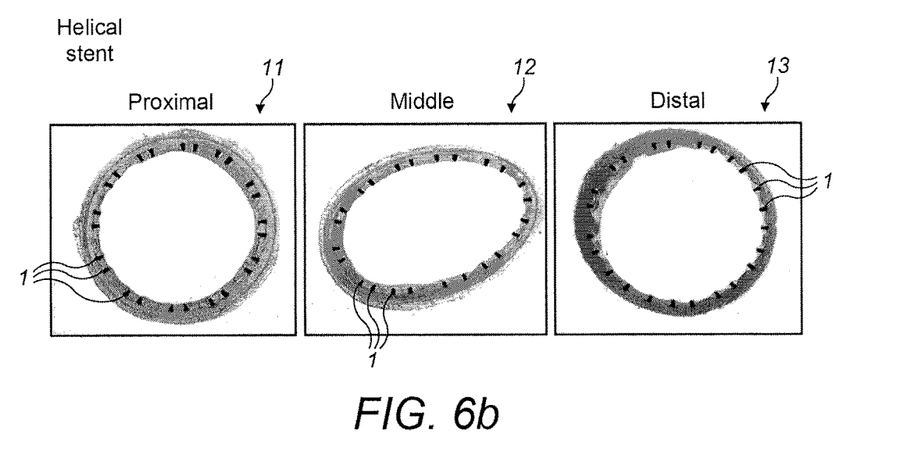

Transverse sections of segments of the carotid arteries one month after implantation are shown in FIG. 6. FIG. 6a shows a proximal section 8, a middle section 9 and a distal section 10 for the straight stented artery 4. FIG. 6b shows a proximal section 11, a middle section 12 and a distal section 13 for the helical stented artery 5.

Figure 9:
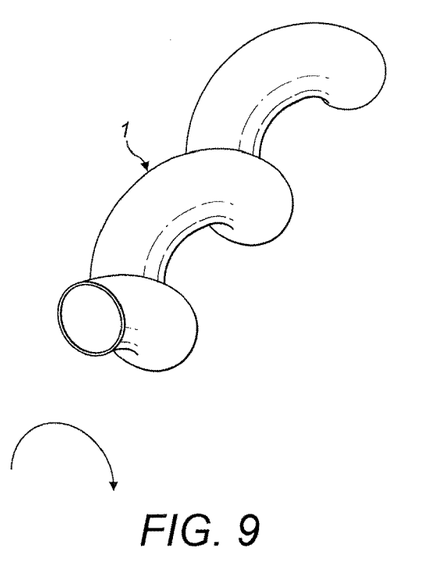
FIG. 9 is a perspective view of a helical stent with right-handed curvature.
Figure 10:
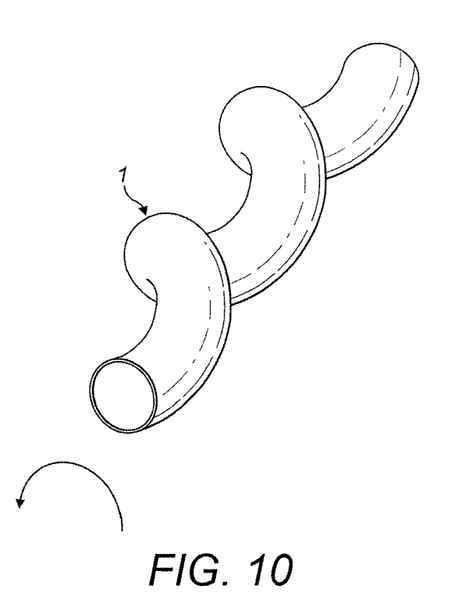
FIG. 10 is a perspective view of a helical stent with left-handed curvature.

FIG. 9 shows a stent 1 with right-handed curvature, for use in a vessel which has been determined to naturally impart right handed swirl flow, and FIG. 10 shows a stent 1 with left-handed curvature for use in a vessel which has been determined to naturally impart left-handed swirl flow. In FIG. 9 an arrow indicates the clockwise, right-handed curvature and in FIG. 10 an arrow indicates the counter clockwise, left-handed curvature. The pair of stents form a kit, or apparatus, from which an appropriate stent may be selected. In such a kit, additional right- and left-handed curvature stents may be provided. When a clinician wishes to stent a vessel, the kit provides a choice of using a right-hand curved stent or a left-hand curved stent. A stent may be selected as appropriate to complement the natural direction of swirl and not to tend to cancel it.

Figure 11:
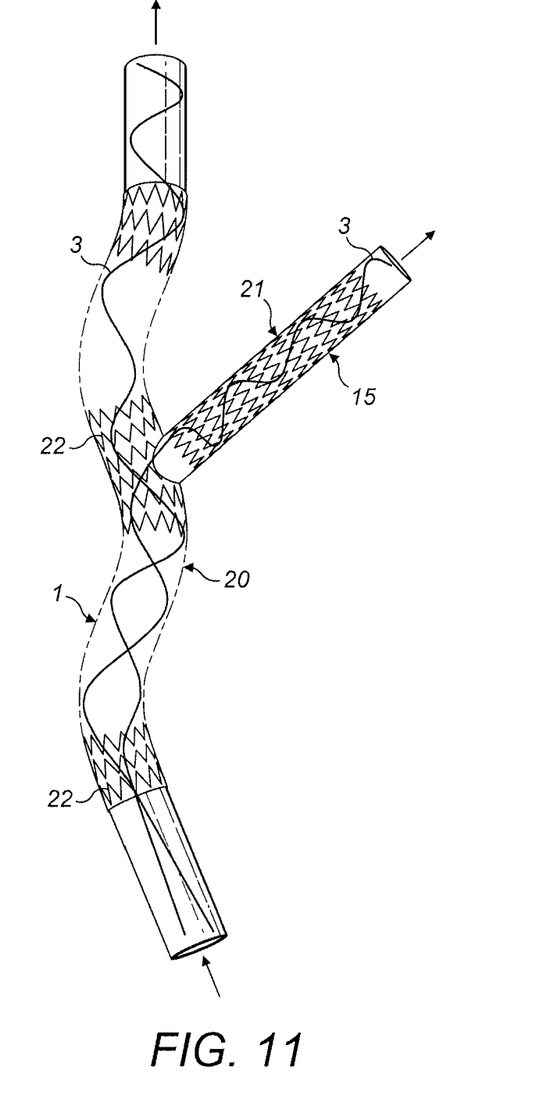
FIG. 11 shows perspective views of a drug eluting helical stent at a vessel branch, with a straight stent in a collateral vessel.

FIG. 11 shows a drug eluting stent 1 having a centre line which curves in three dimensions. The stent has struts 22 and is placed in a main vessel 20. The direction of flow of blood in the main vessel 20 is indicated by the arrows, i.e. the blood inflow is at the lower end of the vessel as seen in the Figure, and the blood outflow is at the upper end of the vessel. Because the stent has a centre line which curves in three dimensions, it imposes a corresponding curved centre line on the main vessel 20. The effect is to promote swirling flow as indicated by the flow lines 3.

A branch vessel 21 branches from the main vessel 22. This is shown stented with a conventional stent 15 having a straight centre line. The secondary flow over the struts 22 which are coated with a drug causes the drug to be moved from the immediate vicinity of each strut to the areas between the struts. This may inhibit intimal growth in those areas, and therefore intimal growth overall. In addition, the drug may be carried by the secondary flow into the branch vessel 21. The stent 15 in the branch vessel is a non-drug eluting stent. However, the drug carried from the main vessel 20 can provide a therapeutic benefit in the branch vessel 21 where it is stented by the stent 15. Finally, the secondary flow in the main vessel may increase the flow into the branch vessel 21 (compared to a situation where the main vessel was stented with a straight stent), promoting secondary flow in the branch vessel and hence providing a therapeutic benefit.

Figure 12:
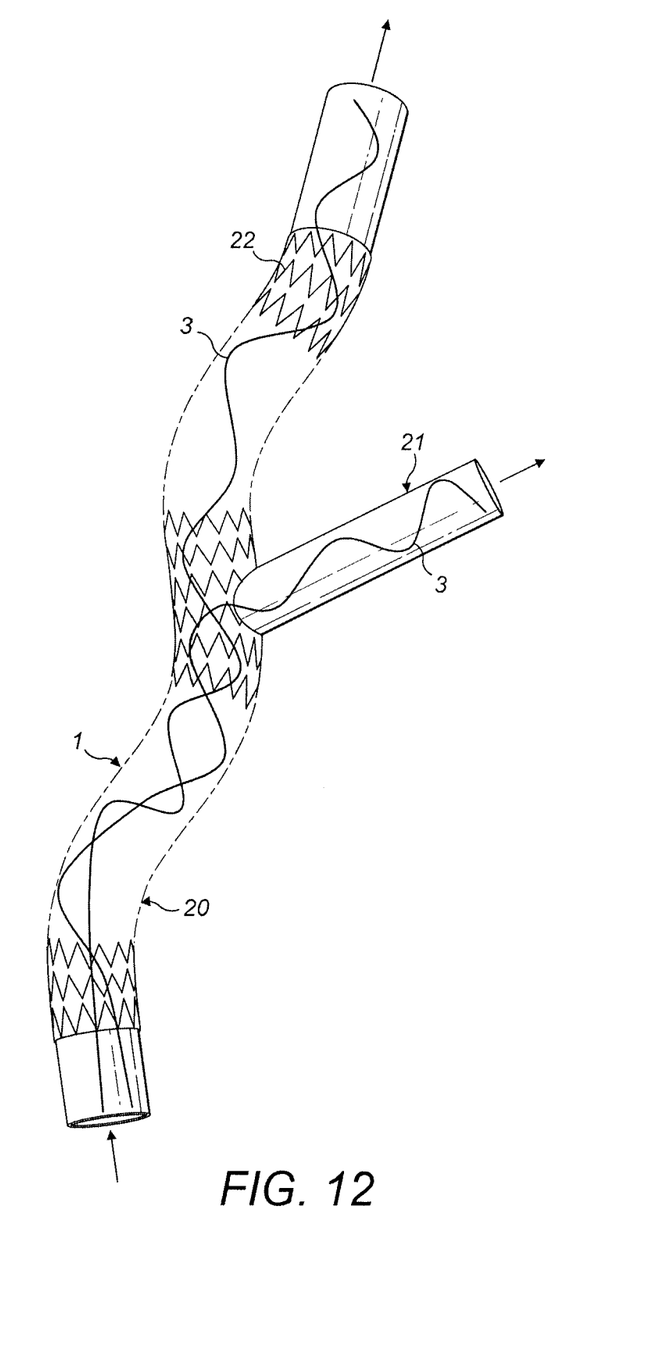
FIG. 12 shows perspective views of a drug eluting helical stent at a vessel branch, without there being any stent in a collateral vessel.

FIG. 12 shows a similar arrangement to FIG. 11, with the difference being that there is no stent in the branch vessel 21. In this case the swirl flow again allows the drug on the struts 22 of the stent 1 in the main vessel 20 to be conveyed to the areas between the struts. The secondary flow in the main vessel assists conveyance of the drug into the secondary vessel, where it may inhibit the development of a stenosis at the proximal end of the branch vessel. The secondary flow in the main vessel may increase the flow generally (irrespective of the presence of the drug) to the branch vessel 20 and thereby also aid perfusion and inhibit stenosis development.

Figure 13:
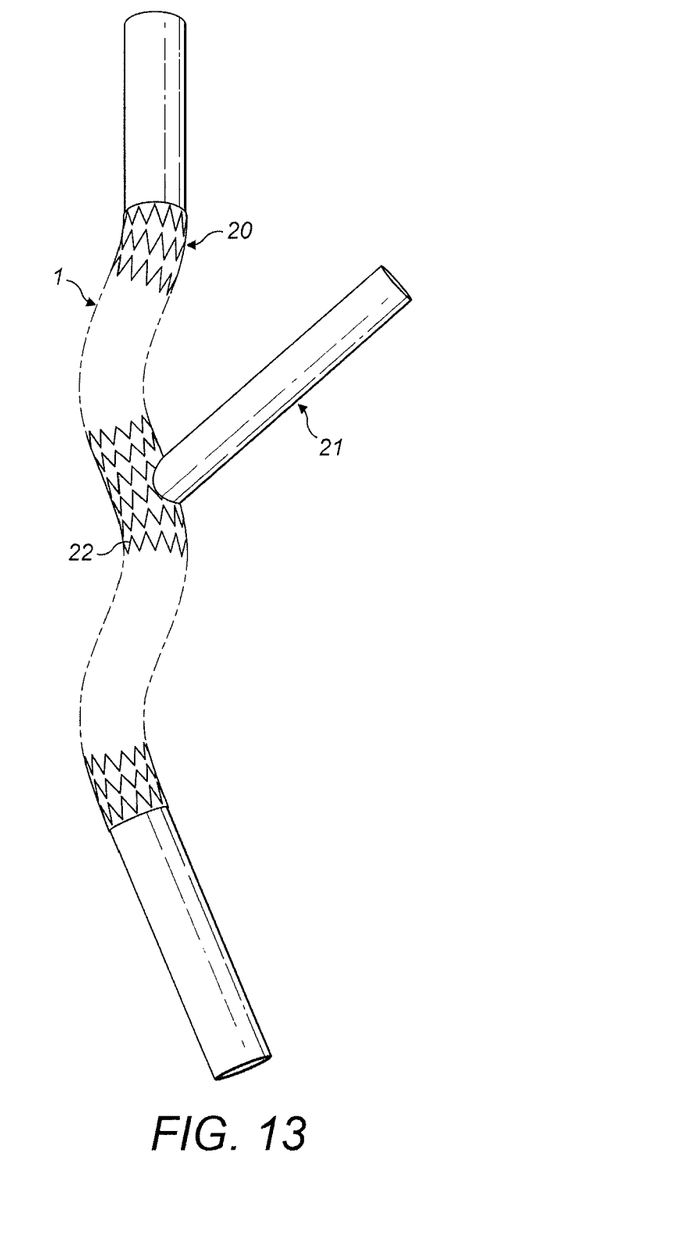
FIG. 13 shows a perspective view of a bare metal helical stent at a vessel branch, without there being any stent in a collateral vessel.

FIG. 13 shows a stent 1 having struts 22 in a main vessel 20. The stent 1 is a bare metal stent (i.e. it is not a drug eluting stent) having a centre line which curves in three dimensions. This increases secondary flow in the main vessel compared to a situation where the main vessel is provided with a straight stent. The secondary flow may act to increase the flow into the branch vessel 21, which may aid perfusion and inhibit stenosis development in the branch vessel 21.

The stent shown in FIG. 13 may be constructed to have a helical geometry when in an expanded condition from the outset. Therefore it may be a balloon expandable stent or a self-expanding stent comprising a shape memory material, in each case being designed to adopt a helical shape when expanded. Alternatively, the stent shown in FIG. 13 may have been already installed in the vessel, and it has then been post dilated using a helical expandable member, such as a balloon, so as to adopt the helical shape shown in FIG. 3. This may provide a way of treating a stenosis which has developed in the branch vessel 21 following the initial straight stent placement in the main vessel 20. The shape of the stent in the main vessel is modified to have a centre line which curves in three dimensions, thereby providing this treatment.

Example

A study was undertaken using ten pigs. In each animal a straight stent was placed in one of the carotid arteries and a helical stent was placed in the contralateral carotid artery. Ultrasound was used to measure the arteries for stent diameter selection and the stents were oversized with respect to the internal artery diameter. Five of the straight stents were deployed in a right artery and five in the left, and five of the helical centre line stents were deployed in the left carotid artery and five in the right carotid artery. Digital subtraction angiography, using a contrast agent, was performed immediately after stent deployment to assess vessel geometry. An example is shown in FIG. 4. In addition, a small bolus of contrast agent was injected intraluminally to assess whether there was swirling. Doppler ultrasound was used to detect swirling flow in the helically stented artery. In the contralateral straight stented vessel, axial passage of the contrast agent was observed.

Implantation of both the straight stent and the helical stent caused immediate deformation of the vessels, but the latter stent caused additional helical deformation of vessels and swirling of intraluminal flow. The changes persisted to the end of the study at 30 days. In fact, the maximum stent amplitude increased from the time of implantation to the time of termination at 30 days.

The amplitude ratio is the helical amplitude divided by the internal diameter of the stent. The average maximum amplitude ratio for the ten helically stented arteries was 0.18 with a standard deviation of 0.11 at implantation and 0.31 with a standard deviation of 0.14 at day 30.

After termination at 30 days transverse sections of proximal (downstream), middle and distal (upstream) segments of the carotid arteries were studied. An example of a straight stented artery, showing these three segments, is shown in FIG. 6a, and an example of a helically stented artery, having these three segments, is shown in FIG. 6b.

Histological study showed the neointima to consist of smooth muscle cells in an organised extra-cellular matrix, with uniform endothelial cell coverage and no difference between the straight centre line stented and helical centre line stented groups, with respect to inflammation, mural thrombosis, or re-endothelialization scorings.

Transverse sections from the proximal, middle and distal segments of the stented carotid arteries showed intimal thickness to be significantly less in the helical centre line stented than straight centre line stented vessels, as seen in FIG. 6. Averaged over the three segments, intimal thickness was 45% lower in the helical centre line stented artery than in the straight centre line stented artery.

In a healthy artery or vein the intima forms the innermost layer. It is made up of one layer of endothelial cells which are in direct contact with the blood flow and internal elastic membrane. Radially outwardly of the intima is a middle layer known as the media. In this example the intima/media thickness ratio was investigated.

Figure 7A:
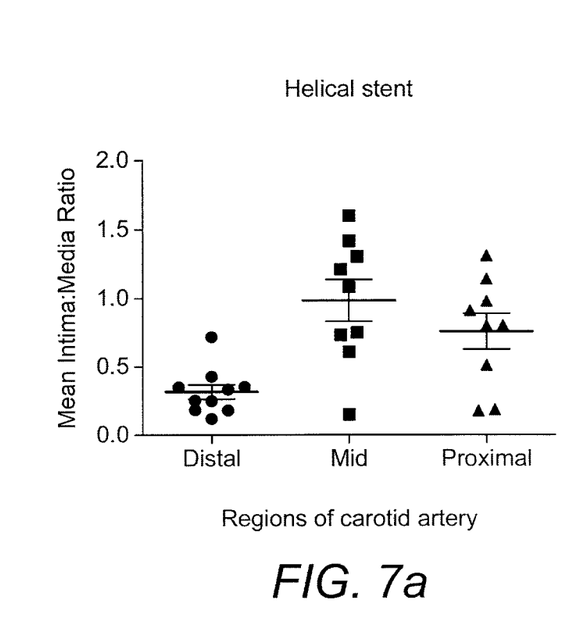
FIGS. 7a and 7b show graphs of intima/media thickness ratios for helical stented and straight stented carotid arteries, respectively.
Figure 7B:
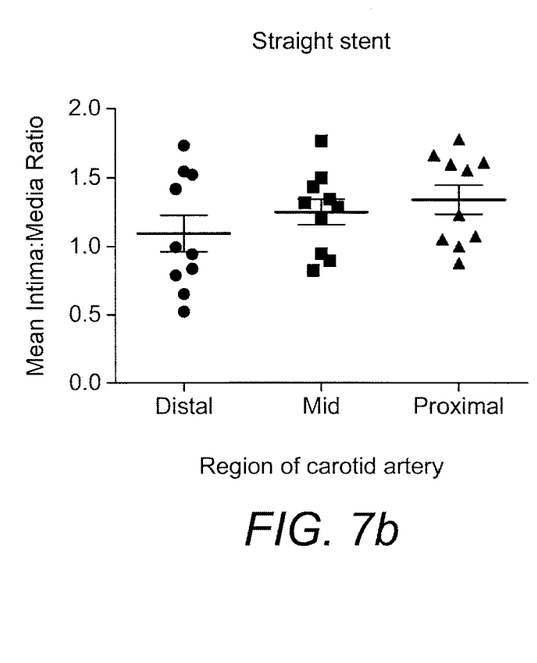

The results are shown in FIG. 7. FIG. 7a shows a graph of intima/media thickness ratios for the helical stented artery and FIG. 7b shows a graph of intima/media thickness ratios for the straight stented artery. Comparing FIG. 7a showing the helically stented artery with FIG. 7b showing the straight stented artery, it will be seen that the intima/media thickness ratio was significantly higher overall in the straight centre line stented than the helical centre line stented vessels. In addition, the ratio was significantly lower in the distal than proximal or middle segments in the helical centre line stented vessels. Thus the histology revealed the intima/media thickness ratio and intimal hyperplasia to be significantly lower in helical centre line stented arteries than in straight centre line stented arteries.

Figure 8A:
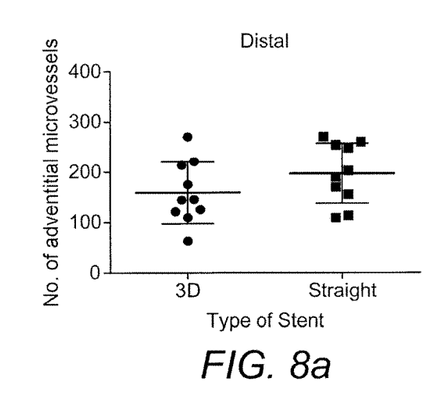
FIGS. 8a to 8d show graphs of adventitial micro vessel counts at distal, middle and proximal locations, and the average of the distal, middle and proximal counts, respectively, for helical stented and straight stented carotid arteries.
Figure 8B:
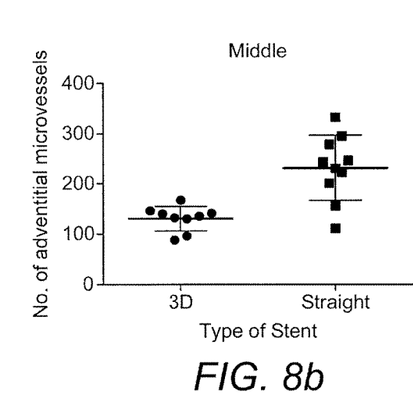
Figure 8C:
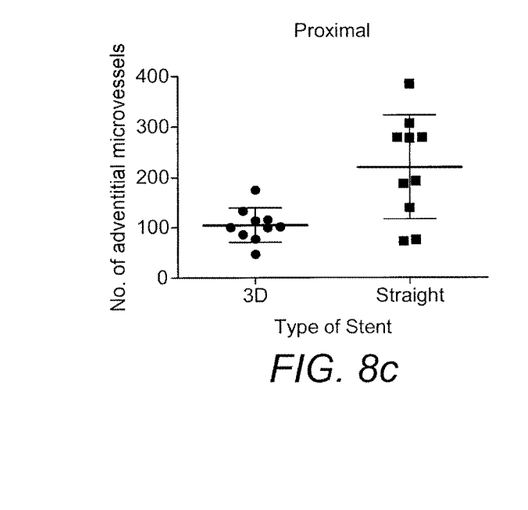
Figure 8D:
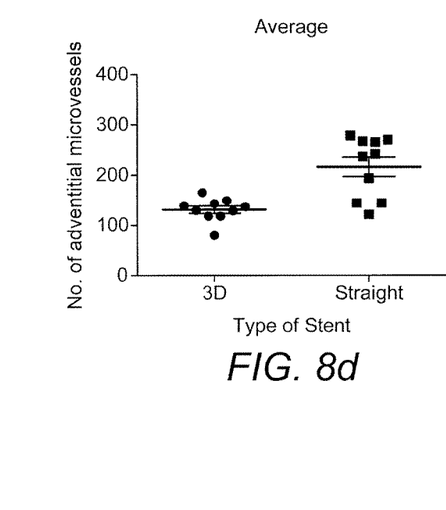

The number of adventitial micro vessels was determined for each sample, for both the helical centre line stented and straight stented arteries. Adventitial micro vessel number was not correlated with section thickness. The results shown in FIG. 8 therefore are presented as adventitial micro vessel density (number of micro vessels per unit adventitial area). FIG. 8a shows a graph of adventitial micro vessel counts at the distal location for the helical (3D) stented and straight stented carotid arteries, FIG. 8b shows a graph of adventitial micro vessel counts at the middle location for the helical (3D) stented and straight stented carotid arteries, FIG. 8c shows a graph of adventitial micro vessel counts at the proximal location for the helical (3D) stented and straight stented carotid arteries, and FIG. 8d shows a graph of the average of the distal, middle and proximal adventitial micro vessel counts, for helical (3D) stented and straight stented carotid arteries. Considering the averaged results for the proximal, middle and distal segments shown in FIG. 8b, adventitial micro vessel density was significantly lower in the helical centre line stented than straight centre line stented arteries, the values being: helical centre line stented 130.8±7.2; straight centre line stented 216.3±19.1. The difference between helical centre line stented and straight centre line stented vessels was pronounced in the proximal and middle segments, but not significant in the distal segments.

It was found that adventitial micro vessel density was significantly lower in the helical centre line stented vessels than in the straight centre line stented arteries. This supports the proposal that adventitial micro vessel density is representative of wall hypoxia. The lesser occurrence of intimal hyperplasia in the helical centre line stented arteries than in the straight centre line stent arteries resulted from improved intraluminal mixing and hence enhanced blood-wall mass transport, thereby reducing the effect of stent-induced wall hypoxia.

We also consider changes in the different (proximal, middle and distal) segments of the straight-and helical centre line stented arteries. The proximal segment is at the upstream end of the artery and the distal segment is at the downstream end. The flow can be expected to develop with distance along both types of stented artery. In the straight centre line case, presuming the vessel to be straight, circular, uniform in cross-section and unbranched, wall shear stress will fall with distance along it, due to the cylindrical shape imposed by the stent and hence the development of a thicker boundary layer where blood flow speeds are slow or even stagnant. In the helical centre line case, the flow will additionally depend on the curvature of the helical vessel and, assuming the diameter and other geometric parameters to remain constant along the vessel, wall shear stress will, in contrast with the straight case, rise with distance as swirl flow develops, with the consequent reduction in the thickness of the boundary layer. Assuming that increase of wall shear stress lessens intimal hyperplasia, the lower intima/media thickness ratio in the distal than proximal and middle segments of the helical centre line stented vessels, as shown in FIGS. 7a and 7b, could, therefore, relate to a rise of wall shear stress associated with development of the flow.

Measurements from angiograms show, however, that both the helical- and straight-stented carotid arteries taper in the downstream direction (the proximal to distal direction), their cross-sectional areas decreasing on average from 24 mm$^2$ to 20 mm$^2$ between the proximal and distal segments. Provided the mass flux remained essentially constant along the vessels, such tapering would increase wall shear stress proceeding downstream and could therefore contribute to explaining the lower intima/media thickness ratio seen in the distal than proximal and middle segments of helical centre line stented carotid arteries. Moreover, it could help explain the tendency for the intima/media thickness ratio to be lower—rather than predicted higher—proceeding from the proximal to distal segments of straight centre line stented vessels, as seen in FIG. 7.

There is, however, evidence supportive of the hypothesis that helical centre line stented carotid arteries were less hypoxic than straight centre line stented vessels, namely that supplementary oxygen reduced the severity of intimal hyperplasia after arterial stenting in animals. It is clear that, whether the section considered is proximal, middle or distal, the density of adventitial micro vessels, which is representative of hypoxia, is greater for straight stented vessels than for helically stented vessels. The average adventitial micro vessel counts shown in FIG. 8d show a higher average adventitial micro vessel density in the straight stented arteries compared to the "helically" stented arteries.

The invention claimed is:

1. A method of treating a subject for whom blood vessel stenting is indicated, comprising:
    identifying a treatment site;
    determining whether natural vessel geometry at that treatment site will impart right-handed swirl flow or left-handed swirl flow to the blood flow along the vessel; and
    selecting for placement at the treatment site a stent having a centre line with three-dimensional curvature;
    the selected stent having right-handed curvature if the vessel has been determined to naturally impart right handed swirl flow and the selected stent having left-handed curvature if the vessel has been determined to naturally impart left-handed swirl flow.

2. A method as claimed in claim 1, wherein the step of determining whether the natural vessel geometry at that treatment site will impart right-handed swirl flow or left-handed swirl flow comprises scanning the vessel, optionally using a method selected from: x-ray scanning transverse colour doppler ultrasound, computer tomography, magnetic resonance imaging, c-arm cone beam CT.

3. A method as claimed in claim 1, wherein it is determined that the treatment site will impart right-handed swirl flow if the vessel is one of: left iliac artery, left iliac vein, left femoropopliteal artery, left femoropopliteal vein, left coronary artery, left anterior descending artery.

4. A method as claimed in claim 1, wherein it is determined that the treatment site will impart left-handed swirl flow if the vessel is one of: right iliac artery, right iliac vein, right femoropopliteal artery, left coronary circumflex, right femoropopliteal vein.

5. A method as claimed in claim 1, further comprising placing the selected stent in the vessel.

6. A method as claimed in claim 5, wherein the selected stent is placed downstream of a bifurcation.

7. A method as claimed in claim 1, wherein the stent when expanded ex vivo has a helical centre line.

8. A method as claimed in claim 1, wherein the stent comprises a shape memory material, optionally nitinol.

9. A method as claimed in claim 1, wherein the stent comprises a plastically deformable material.

10. A method as claimed in claim 5, further comprising expanding the stent in the vessel with the aid of a balloon.

* * * * *